United States Patent [19]

Matsuura et al.

[11] Patent Number: 5,229,293

[45] Date of Patent: Jul. 20, 1993

[54] RECOMBINANT BACULOVIRUS

[75] Inventors: Yoshiharu Matsuura, 5-3, Hikaricho-3-chome, Kokubunji-shi; Kotaro Yasui, Tachikawa; Takanori Sato, Yokohama, all of Japan

[73] Assignees: Nippon Zeon Co Ltd.; Tokyo Metropolitan Institute for Neurosciences, both of Tokyo; Yoshiharu Matsuura, Kokubunji, all of Japan

[21] Appl. No.: 349,560

[22] Filed: May 5, 1989

[30] Foreign Application Priority Data

May 12, 1988 [JP] Japan .................. 63-115316

[51] Int. Cl.$^5$ .............................. C12N 15/86
[52] U.S. Cl. .................. 435/320.1; 435/69.1
[58] Field of Search ............ 435/69.3, 320.1; 536/27

[56] References Cited

U.S. PATENT DOCUMENTS 4,745,051  5/1988  Smith .

FOREIGN PATENT DOCUMENTS

| 0228036 | 7/1987 | European Pat. Off. . |
| 0251467 | 1/1988 | European Pat. Off. . |
| 0260090 | 3/1988 | European Pat. Off. . |
| 0265785 | 5/1988 | European Pat. Off. . |
| 2620459 | 3/1989 | France . |
| 88/02030 | 3/1988 | PCT Int'l Appl. . |
| 2191201 | 12/1987 | United Kingdom . |
| 2226031 | 6/1990 | United Kingdom . |

OTHER PUBLICATIONS

Luckow et al., Bio/Technology, vol. 6, Jan. 1988, pp. 47-55.
Virology, 52, 456-467 (1973).
Journal of Virologyo, 19, 820-832 (1976).
Virology, 89, 517-527 (1978).
J. Gen Virol., 40, 531-544 (1978).
Science, 219, 715-721 (1983).
Virology, 131, 561-565 (1983).
Journal of Virology, 45, 215-225 (1983).
Molecular and Cellular Biology, 3, 2156-2165 (1983).
Science, 229, 726-733 (1985).
Gene, 48, 195-201 (1986).
Virology, vol. 173, No. 4, "Characterization of Japanese Encephalitis Virus Envelope Protein Expressed by Recombinant Baculorviruses".
Tropical Medicine, vol. 29, No. 4, "Expression of envelope glycoprotein E of Japanese Encephalitis Virus using Bombyx mori Nuclear Polyhedrosis Virus".
J. Viral 1988, 62(8), 3027-3031.
Vaccines 1987, 87, 382-388.
J. Cell, Biochem, 1987, 11C, 172 (Abstract M017).
Proc. Natl. Acad. Soc. USA 1985, 82, 8404-8408.
Mol. Cell. Biol. 1984, 4(3), 399-406.
Mol. Cell. Biol. 1983, 3, 2156-2165.

Primary Examiner—Richard A. Schwartz
Assistant Examiner—David Guzo
Attorney, Agent, or Firm—Nikaido, Marmelstein, Murray & Oram

[57] ABSTRACT

Recombinant Baculovirus in which the cDNA encoding E protein derived from Japanese encephalitis virus is integrated into the genome region non-essential to proliferation of Baculovirus under control of the promoter is infected to insect cells such as Sf9 cells, derived from *Spodoptera frugiperda* and the infected cells are cultured to express E protein of Japanese encephalitis. This E protein is useful as vaccines or diagnostics.

6 Claims, 12 Drawing Sheets

FIG. 1

```
                         pUC8
GENOME      EcoR I-I FRAGMENT
DNA OR    ─────────────────→ ○    PRODUCTION OF FIRST
AcNPV                              RECOMBINANT VECTOR
         JAPANESE                  (CF. FIGS. 5,6,7)
         ENCEPHALITIS
         VIRUS cDNA
                            ↓
                            ○    PRODUCTION OF SECOND
                                  RECOMBINANT VECTOR
                                  (CF. FIG. 8)
```

↓ $Ca^{++}$ COPPECIPITATION

↓ TRANSFECTION TO Sf 9 CELL

↓ MEDIUM (VIRUS MASS)

↓ SELECTION OF RECOMBINANT VIRUS

↓ PURIFICATION

RECOMBINANT VIRUS AcJ3

↓ INFECTED TO Sf 9 CELL

↓ CULTURING UNDER OPTIMUM CONDITIONS

↓ HOMOGENIZATION OF CELLS

↓ PURIFICATION OF ANTIGEN PROTEIN OF JAPANESE ENCEPHALITIS

E PROTEIN OF JAPANESE ENCEPHALITIS

```
     -244
      ↓                                                                                    -227
    ATC ACG TTC TTC AAG TTT ACA GCA TTA GCC CCG ACC AAG GCG CTT TTA GGC CGA
    Ile Thr Phe Phe Lys Phe Thr Ala Leu Ala Pro Thr Lys Ala Leu Leu Gly Arg
     2-20
                                                                                           -209
    TGG AAA GCA GTG GAA AAG AGT GTG GCA ATG AAA CAT CTT ACT AGT TTC AAA CGA
    Trp Lys Ala Val Glu Lys Ser Val Ala MET Lys His Leu Thr Ser Phe Lys Arg
                                                                                           -191
    GAA CTT GGA ACA CTC ATT GAC GCC GTG AAC GCC AGA AAA CAA AAC AAA
    Glu Leu Gly Thr Leu Ile Asp Ala Val Asn Ala Arg Gly Lys Gln Asn Lys
                                                                                           -173
    AGA GGA AAT GAA GGC TCA ATC ATG TGG CTC GCA AGC TTG GCA GTT GTC ATA
    Arg Gly Asn Glu Gly Ser Ile MET Trp Leu Ala Ser Leu Ala Val Val Ile
                      ┌─PreM                    HindIII
                     -167                                                                  -155
    GCT TAC GCA GGA GCA ATG AAG TTG TCG AAT TTC CAG GGG AAG CTT TTG ATG ACC
    Ala Tyr Ala Gly Ala MET Lys Leu Ser Asn Phe Gln Gly Lys Leu Leu MET Thr
                                                                                           -137
    ATC AAC AAC ACG GAC ATT GCA GAC GTT ATC CTG ATT CCC ACC TCA AAA GGA GCG
    Ile Asn Asn Thr Asp Ile Ala Asp Val Ile Leu Ile Pro Thr Ser Lys Gly Ala
                                                                                           -119
    AAC ATA TGC TGG GTC CGG GCA ATA GAC GTC GGC TAC ATG TGT GAG GAC ACT ATC
    Asn Ile Cys Trp Val Arg Ala Ile Asp Val Gly Tyr MET Cys Glu Asp Thr Ile
                                                                                           -101
    ACG TAC GAA TGT CCT AAG TTC ACC ATG GGC AAT GAT CCA GAG GAT GTG GAT TGT
    Thr Tyr Glu Cys Pro Lys Phe Thr MET Gly Asn Asp Pro Glu Asp Val Asp Cys
                                                                                           -83
    CGG TGT GAC AAC CAA GAA GTC TAC GTC TAC GTC AAA TAT GGC CGG TGC ACG CGG AGG
    Arg Cys Asp Asn Gln Glu Val Tyr Val Tyr Val Lys Tyr Gly Arg Cys Thr Arg
              M
                                                                                           -65
    CAT TCC AAG CGA AGC AGG AGA TCC GTG TCG CAA ACA CAT GGG GAG AGT TCA
    His Ser Lys Arg Ser Arg Arg Ser Val Ser Gln Thr His Gly Glu Ser Ser
```

FIG. 4(2)

```
CTA GTG AAT AAA GAG GCT TGG CTG GAT TCA ACG AAA GCC ACA CGG TAT CTC                              -47
Leu Val Asn Lys Glu Ala Trp Leu Asp Ser Thr Lys Ala Thr Arg Tyr Leu

ATG AAA ACT GAG AAC TGG ATC ATA AGG AAC AAC AAT CCT GGC TAT GCT CTG TCT CTG GCG GCG              -29
MET Lys Thr Glu Asn Trp Ile Ile Arg Asn Asn Asn Pro Gly Tyr Ala Leu Ser Leu Ala Ala

GTA CTT GGC TGG ATG CTT GGC AGT CAA CAA AAT CCT GGT GTA TTT ACC ATC                              -11
Val Leu Gly Trp MET Leu Gly Ser Gln Gln Asn Pro Gly Val Phe Thr Ile
                                        -1  +1
                                         ──E──

CTC CTG CTG GTC GCT TAC CCG GCT TTT AAT TGT CTG GGA ATG GGC AAT                                   +8
Leu Leu Leu Val Ala Tyr Pro Ala Phe Asn Cys Leu Gly MET Gly Asn

CGT GAC TTC ATA GAA GGA GCC AGT GGA GCC ACT TGG GTG GTG GAC TTG GTG CTA GAA                      +26
Arg Asp Phe Ile Glu Gly Ala Ser Gly Ala Thr Trp Val Val Asp Leu Val Leu Glu
                                                                      4118

GGA GAT AGC TGC TTG ACA ATC ATG GCA AAC CAA CTT GCT GAG GTC AGA AGT TAC TGC TAT CAT              +44
Gly Asp Ser Cys Leu Thr Ile MET Ala Asn Gln Leu Ala Glu Val Arg Ser Tyr Cys Tyr His
                                                                                AqtII
                                                                            GAC GTC CGC +62
                                                                            Asp Val Arg

ATG ATT AAC ATC GAA GCT AGC ACG GTG GCT ACG AGC TAT GTG TGC AAA CCC ACG ACT GGA GAA GCC          +80
MET Ile Asn Ile Glu Ala Ser Thr Val Ala Thr Ser Tyr Val Cys Lys Pro Thr Thr Gly Glu Ala

GCT TCA GTC ACT GAC ATC GAT GCT GAT AGC TAT AGT AGC CAA CTT TCA AAT GGC TTC ACT GAT              +98
Ala Ser Val Thr Asp Ile Asp Ala Asp Ser Tyr Ser Ser Gln Leu Ser Asn Gly Phe Thr Asp
                                                                               2-20   +116

CAC AAC GAG AAG CGA AAG CGA ATC ATG ACG AGC TAT AGT ACG CCC AGC AGC CCG ACT ACG AAA CAA GGC TTC ACT GAT
His Asn Glu Lys Arg Lys Arg Ile MET Thr Ser Tyr Ser Thr Pro Ser Ser Pro Thr Thr Lys Gln Gly Phe Thr Asp

CGT GGG TGG GGC AAC GGA TGT GGA CTT TTC GGG AAG GGA AGC ATT GAC ACA TGT
Arg Gly Trp Gly Asn Gly Cys Gly Leu Phe Gly Lys Gly Ser Ile Asp Thr Cys
```

FIG.4(3)

```
                                                                              +134
GCA AAA TTC TCC TGC ACC AGC AAA GCG ATT GGA AGA ACA ATC CAG CCA GAA AAC
Ala Lys Phe Ser Cys Thr Ser Lys Ala Ile Gly Arg Thr Ile Gln Pro Glu Asn
                                                                              +152
ATC AAA TAC GAA GTT GGC ATT TTT GTG CAT GGA ACC ACT TCG GAA AAC CAT
Ile Lys Tyr Glu Val Gly Ile Phe Val His Gly Thr Thr Ser Glu Asn His
                                                                              +170
GGG AAT TAT TCA GCG CAA GTT GGG GCG TCC CAG GCG GCA AAG TTC ACA GTA ACA
Gly Asn Tyr Ser Ala Gln Val Gly Ala Ser Gln Ala Ala Lys Phe Thr Val Thr
                                                                              +188
CCC AAT GCT CCT TCG ATA ACC CTC AAA CTT GGT GAC TAC GGA GAA GTC ACG CTG
Pro Asn Ala Pro Ser Ile Thr Leu Lys Leu Gly Asp Tyr Gly Glu Val Thr Leu
                                                                              +206
GAC TGT GAG CCA AGA AGT GGA CTG AAC ACT GAA GCG TTT TAC GTC ATG ACC GTG
Asp Cys Glu Pro Arg Ser Gly Leu Asn Thr Glu Ala Phe Tyr Val MET Thr Val
                                                                              +224
GGG TCA AAG TCA TTT CTG GTC CAT AGG GAA TGG TTT CAT GAC CTC GCT CTC CCC
Gly Ser Lys Ser Phe Leu Val His Arg Glu Trp Phe His Asp Leu Ala Leu Pro
                                                                              +242
TGG ACG TCC CCT TCG AGC ACA GCC ACA AAA CAG TCC GCT GTT GCT CTT ATG GAA TTT
Trp Thr Ser Pro Ser Ser Thr Ala Thr Lys Gln Ser Ala Val Ala Leu MET Glu Phe
                                                                              +260
GAA GAG GCG CAC GCC GCA AAA CAG TCC GCT GTT GCT CTT GGG TCA CAG GAA GGA
Glu Glu Ala His Ala Ala Thr Lys Gln Ser Ala Val Ala Leu Gly Ser Gln Glu Gly
                                                                              +278
GGC CTC CAT CAG GCG TTG GCA GGA GCC ATC GTG GTG GAG TAC TCA AGC TCA GTG
Gly Leu His Gln Ala Leu Ala Gly Ala Ile Val Val Glu Tyr Ser Ser Val
                                                                              +296
AAG TTA ACA TCA GGC CAC CTG AAA TGT AGG CTG AAA ATG GAC CCC CTG AAG TTG
Lys Leu Thr Ser Gly His Leu Lys Cys Arg Leu Lys MET Asp Pro Leu Lys Leu
```

```
AAA GGC ACT ACG TAC GGC ATG TGT ACA GAA AAA TTC TCG GCG AAA AAT TCG   +314
Lys Gly Thr Thr Tyr Gly MET Cys Thr Glu Lys Phe Ser Ala Lys Asn Ser

GCA GAC ACT GGC CAC GGA ACA GTC ATT GAA CTA TCC TAC TCT GGG AGT GAT   +332
Ala Asp Thr Gly His Gly Thr Val Ile Glu Leu Ser Tyr Ser Gly Ser Asp
                                                                      +350
GGC CCC TGC AAA ATT CCA GTC TCC GTT GCG AGC CTC AAT GAC ATG ACC CTG
Gly Pro Cys Lys Ile Pro Val Ser Val Ala Ser Leu Asn Asp MET Thr Leu
                                                                      +368
GTT GGC CGG CTG GTG ACA GTG AAC CCT TTC TGC GCG ACT TCC AGT GCC TCA
Val Gly Arg Leu Val Thr Val Asn Pro Phe Cys Ala Thr Ser Ser Ala Ser
                                                                      +386
AAG GTG CTG GTC GAG ATG GAA CCC CCC TTC GGA GAC TCC TAC ATC GTG GTT
Lys Val Leu Val Glu MET Glu Pro Pro Phe Gly Asp Ser Tyr Ile Val Gly
                                                                      +404
TGG GGA GAC AAG CAG ATC AAC CAC CAT TGG CAC AAA GCT GGA AGC AGC GCT
Trp Gly Asp Lys Gln Ile Asn His His Trp His Lys Ala Gly Ser Ser Ala
                                                                      +422
AAG GCC TTT TCA ACA ACT TTG AAG GGA GCT CAA AGA CTG GCA GCG TTG GAC
Lys Ala Phe Ser Thr Thr Leu Lys Gly Ala Gln Arg Leu Ala Ala Leu Gly
                                                                      +440
ACA GCC TGG GAC TTT GGC TCC ATT GGA GGG GTC TTC AAC TCC ATA GGA AAA GCC
Thr Ala Trp Asp Phe Gly Ser Ile Gly Gly Val Phe Asn Ser Ile Gly Lys Ala
                                                                      +458
GTT CAC CAA GTG TTT GGT GGC TTC GCC TTC AGA ACA CTC TTT GGG ATG TCT TGG
Val His Gln Val Phe Gly Gly Phe Ala Phe Arg Thr Leu Phe Gly MET Ser Trp
                                                                      +476
ATC ACA CAA GGG CTA ATG GGT GCC CTA CTC CTA CTC TGG ATG GGC GTC AAC GCA CGA
Ile Thr Gln Gly Leu MET Gly Ala Leu Leu Leu Leu Trp MET Gly Val Asn Ala Arg
```

```
                                                                                    +494
GAC CGA TCA ATT GCT TTG GCC TTC TTA GCC ACA GGA GGT GTG CTC GTG TTC TTA
Asp Arg Ser Ile Ala Leu Ala Phe Leu Ala Thr Gly Gly Val Leu Val Phe Leu
                    E  +500                                                         +512
GCG ACC AAT GTG CAT GCT GAC ACT GGA TGT GCC TTT GAC ATC ACA AGA AAA GAG
Ala Thr Asn Val His Ala Asp Thr Gly Cys Ala Phe Asp Ile Thr Arg Lys Glu
                                                                                    +530
ATG AGA TGT GGA AGT GGC ATC TTT GTG CAC AAC GAC GTG GAA GCC TGG GTG GAC
MET Arg Cys Gly Ser Gly Ile Phe Val His Asn Asp Val Glu Ala Trp Val Asp
                                                                                    +545
AGG TAT AAA TAC TTG CCA GAA ACG CCC AGA TCC CTA GCG AAG ATC GTC CAC AAA
Arg Tyr Lys Tyr Leu Pro Glu Thr Pro Arg Ser Leu Ala Lys Ile Val His Lys
                                                                                    +566
GCG CAC AAG GAA GGC GTG TGC GGA GTC AGA TCT GTC ACT AGA TTG GAG CAC CAA
Ala His Lys Glu Gly Val Cys Gly Val Arg Ser Val Thr Arg Leu Glu His Gln
                                                                                    +584
ATG TGG GAA GCC GTA CGG GAC GAA TTG AAC GTC CTG CTC AAA GAG AAT GCA GTG
MET Trp Glu Ala Val Arg Asp Glu Leu Asn Val Leu Leu Lys Glu Asn Ala Val
                                                   EcoRV                            +602
GAC CTC AGT GTG GTT GTG AAC AAG CCC GTG GGA AGA TAT CGC TCA GCC CCT AAA
Asp Leu Ser Val Val Val Asn Lys Pro Val Gly Arg Tyr Arg Ser Ala Pro Lys
                                                                                    +620
CGC CTA TCC ATG ACG CAA GAG AAG TTT GAA ATG GGC TGG AAA GCA TGG GGG AAA
Arg Leu Ser MET Thr Gln Glu Lys Phe Glu MET Gly Trp Lys Ala Trp Gly Lys
                                                                                    +638
AGC ATT CTC TTT GCC CCG GAA TTG GCT AAC TCC ACA TTT GTC GTA GAT GGA CCT
Ser Ile Leu Phe Ala Pro Glu Leu Ala Asn Ser Thr Phe Val Val Asp Gly Pro
                                                                                    +656
GAG ACA AAG GAA TGC CCT GAT GAG AAT AGA GCT TGG AAC AGC ATG CAA ATC GAA
Glu Thr Lys Glu Cys Pro Asp Glu Asn Arg Ala Trp Asn Ser MET Gln Ile Glu
                                                                                    +674
GAC TTC GGC TTT GGC ATC ACA TCA ACC CGT GTG TGG CTG AAA ATT AGA GAG GAG
Asp Phe Gly Phe Gly Ile Thr Ser Thr Arg Val Trp Leu Lys Ile Arg Glu Glu
                                                                                    +692
AGC ACT GAC GAG TGT GAT GGA GCG ATC ATA GGC ACG GCT GTC AAA GGA CAT GTG
Ser Thr Asp Glu Cys Asp Gly Ala Ile Ile Gly Thr Ala Val Lys Gly His Val
                                                                                    +710
GCA GTC CAT AGT GAC TTG TCG TAC TGG ATT GAG AGT CGC TAC AAC GAC ACA TGG
Ala Val His Ser Asp Leu Ser Tyr Trp Ile Glu Ser Arg Tyr Asn Asp Thr Trp
                                                              Ball  +726
AAA CTT GAG AGG GCA GTC TTT GGA GAG GTC AAA TCT TGC ACT TGG CCA
Lys Leu Glu Arg Ala Val Phe Gly Glu Val Lys Ser Cys Thr Trp Pro
```

RECOMBINANT BACULOVIRUS

BACKGROUND OF THE INVENTION

1. Field of the Invention

The present invention relates to a recombinant Baculovirus having integrated at least a part of cDNA encoding envelope protein of Japanese encephalitis virus into a genome non-essential to proliferation of Baculovirus, a process for efficiently producing envelope protein of Japanese encephalitis virus using said recombinant Baculovirus and a vaccine for Japanese encephalitis virus.

2. Statement of the Prior Art

As a Japanese encephalitis vaccine, there has been hitherto used a vaccine containing inactivated Japanese encephalitis virus as an effective ingredient. The stock solution of inactivated Japanese encephalitis virus vaccine is produced by inoculating Japanese encephalitis virus Nakayama strain found in the National Institute of Health into newborn mice intra-cerebrally, collecting brains from infected mice purifying by the alcohol protamine method and inactivating virus ["Vaccine of Japan", revised second edition, edited by National Institute of Health Alumini Association (published Jan. 20, 1977 by Maruzen Publishing Co., Ltd.)].

In such a vaccine producing process, Japanese encephalitis virus itself must be handled in large quantities so that the handling was extremely highly dangerous to workers in producing vaccines and production costs were also high.

As a vaccine, antigenic protein having viral antigenicity may also be used, not the virus per se. So it has been investigated to produce the antigenic protein in procaryotic cells or eucaryotic cells using recombinant DNA technique. An attempt has also been made to express envelope protein (hereafter sometime referred to as E protein) of Japanese encephalitis virus by genetic manipulation using yeast as a host (Preliminary Abstract of the 34th Meeting of the Japanese Virus Society held in October 1986, page 91). However, expression of natural E protein was unsuccessful.

The present inventors recently succeeded in expressing natural E protein of Japanese encephalitis virus by the recombinant vaccinia virus integrated cDNA encoding E protein into the genome of vaccinia virus used as a live vaccine. Although the recombinant virus is promising as a live vaccine, it involved a problem that its yield was too small to recover the expressed proteins and to use them for the purpose of vaccination or diagnosis.

On the other hand, methods for expressing an exogenous gene in insect cells using an insect viral vector [Japanese Patent Application KOKAI (the term "KOKAI" is used to mean an unexamined application laid open to public inspection) Nos. 37988/1985 and 5787/1986]have been proposed. It is reported that the amount of protein expressed in these methods is markedly higher than that in the other expression systems.

However, Japanese encephalitis virus belonging to the genus Flavivirus of Togaviridae is characterized in that it has a single stranded RNA genome and that a single long polypeptide monocistronically translated from the genome in virus-infected cells undergoes processing (which is used to mean that a single polypeptide is cleaved with protease in cells to form the respective proteins)into capsid protein, membrane protein, E protein and 5 kinds of non-structural proteins; it is thus difficult in its manipulation to integrate cDNA encoding E protein into Baculovirus genome and express E protein. Therefore, no report has yet been made on an example of the expression.

In view of the prior art described above, the present inventors have made extensive investigations on a process for producing E protein of Japanese encephalitis virus in large quantities and as a result, have found that by selecting a region encoding E protein from cDNA prepared from genome RNA of Japanese encephalitis virus, ligating said region encoding E protein with a promoter of Baculovirus and integrating the ligation product into a genome region non-essential for proliferation of Baculovirus, large quantities of Japanese encephalitis virus E protein utilizable as vaccines or diagnostics can be expressed in infected insect cells. Based on this finding, the present invention has come to be accomplished.

SUMMARY OF THE INVENTION

According to the present invention, there are provided a recombinant Baculovirus harbouring cDNA encoding E protein of Japanese encephalitis virus into a genome region non-essential to proliferation of Baculovirus, a process for producing E protein of Japanese encephalitis virus which comprises infecting the insect cell with said recombinant virus, culturing the insect cell and recovering the expressed Japanese encephalitis virus E protein, and a recombinant Baculovirus usable for said process and a vaccine for Japanese encephalitis virus.

DETAILED DESCRIPTION OF THE PREFERRED EMBODIMENTS

In the present invention, any virus is usable as the one provided for production of recombinant virus so long as it is classified into Baculovirus. Examples include *Autographa californica, Trichoplusia ni, Rachiplusia ou, Galleria mellonella, Bombyx mori*, etc. Of these viruses, *Autographa californica* (hereafter simply referred to as AcNPV) is preferred. These viruses have been widely investigated so far and their samples can be obtained from many sources including Texas Agricultural Experiment Station & Extension Service of Texas A & M University, U.S.A.

Further, cDNA encoding envelope protein of Japanese encephalitis virus can be prepared using above-described Nakayama strain found in the National Institute of Health, JaOAr strain (Arboviruses Research Unit of Yale College, Connecticut, U.S.A.), or Sagayama strain (same college).

Figure 4:
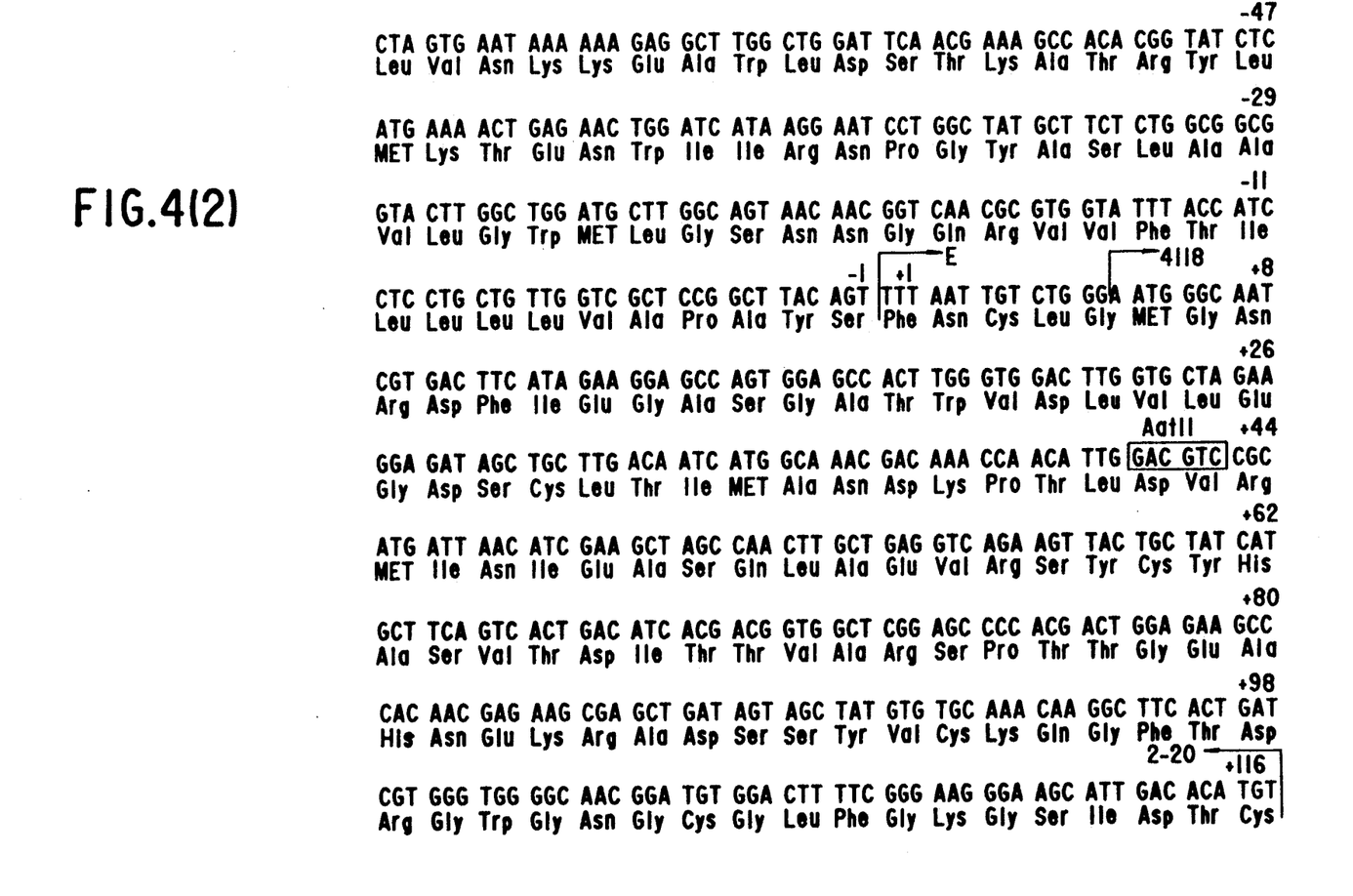
FIG. 4 (parts 1-5) shows base sequence and amino acid sequence of cDNA containing a region encoding E protein.

For example, cDNA encoding E protein which is prepared from Sagayama strain described above is composed of 1500 base pairs in total as shown in FIG. 4. In the present invention, cDNA may also be modified (namely, its base sequence is replaced, inserted or deleted) within a range that has substantially the same function as in the aforesaid cDNA. Of course, cDNA may also be modified to such an extent that its amino acid sequence is modified so long as it has substantially the same function.

In the production of recombinant virus, a first recombinant vector having therein a DNA region which is not essential to proliferation of Baculovirus is firstly constructed. In this case, it is required that a promoter functioning in Baculovirus be present in the region described above. It is further preferred to insert a synthetic linker containing an appropriate restriction enzyme cleavage sequence downstream the promoter.

The DNA region which is not essential to proliferation as used herein refers to a region such as polyhedrin gene of Baculovirus (L.K. Miller, et al., Science, 219, 715-721 (1983)) or the like, that does not substantially affect proliferation of virus even though the region undergoes mutation by insertion of exogenous DNA.

For reference, it is reported that polyhedrin is a protein having a molecular weight of about 29,000 daltons and its gene is present on EcoR I-I fragment of AcNPV genome (G.E. Smith, et al., J. Virol., 45, 215-225 (1983)). DNA sequence of polyhedrin gene is shown in the monograph authored by G.E. Smith, et al. (Virology, 131, 561-565 (1983)).

Further any promoter is usable as the promoter functioning in Baculovirus, irrespective of synthetic or natural one, so long as it can be effectively functioned as a promoter in the transcription system of Baculovirus. Specific examples are a promoter of polyhedrin gene of Baculovirus, a promoter of 10K polypeptide gene of Baculovirus, etc.

The production of the first recombinant vector can be carried out in a conventional manner (for example, Japanese Patent Application KOKAI Nos. 37988/1985 and 5787/1986, etc.). For example, the procedure proceeds as follows. DNA fragment bearing polyhedrin gene is isolated from Baculovirus AcNPV and purified. Then, digestion with EcoR I restriction endonuclease gives 7.3 kilobase EcoR I-I fragment containing polyhedrin gene and other appropriate fragments. The EcoR I-I fragment is cloned to a suitable cloning plasmid at the EcoR I site.

In the case of this system, the promoter of polyhedrin gene is present in the non-essential region. This promoter effectively functions also in a second recombinant vector.

In order to increase the expression level, it is preferred to use a vector, which has a restriction enzyme site immediately after promoter and 5' non-translational region of polyhedrin gene followed by 3' non-translational region of polyhedrin gene, but lacks the coding sequence of polyhedrin gene. It is reported that such a vector causes an extremely high expression level of an exogenous gene (Matsuura et al., J. gen. Virol., 68, 1233-1250 (1987)).

As has been stated hereinbefore, protein of Japanese encephalitis virus is monocistronically synthesized and then processed to separate into envelope protein, etc. Accordingly, when cDNA for the entire virus genome is inserted, it is unnecessary to insert translation initiation codon and translation termination codon artificially. This also applies to the case that cDNA to be inserted contains at its upstream a sequence (e.g., ATG) capable of acting as translation initiation codon, in addition to the region for encoding E protein. When cDNA encoding E protein alone is above integrated, it is necessary to integrate a synthetic linker having translation initiation codon, translation termination codon and a restriction enzyme sites between the two codons into the restriction enzyme site as the downstream of promoter.

The translation termination codon to be inserted is desirably provided at 3 positions by shifting the reading frame so as to be in accord with the reading frame of cDNA encoding E protein, whichever it is.

The cDNA to be inserted may also be cDNA containing a region for encoding any additional protein, so long as it contains the region for encoding E protein. In Flavivirus, a region encoding a membrane protein (hereafter referred to as M protein), a premembrane protein (hereafter referred to as preM protein) and a capsid protein (hereafter referred to as C protein) are present at the upstream in the region for encoding E protein. In the present invention, there may also be used a virus in which all or a part of cDNAs encoding these proteins may be linked to the cDNA encoding E protein at the upstream thereof.

Specific examples of the used vector include plasmids such as pBR322, pBR325, pBR327, pBR328, pUC7, pUC8, pUC9, pUC19 and the like; phages such as λ phage, M13 phage and the like; cosmids such as pHC79 (Gene, 11, 291, 1980), etc.

In the present invention, the region for encoding E protein of Japanese encephalitis virus is then inserted at the downstream of the promoter of the first recombinant vector thereby to construct a second recombinant vector. The method for insertion may also be performed in a conventional manner (e.g., cf. the patent publications supra); for example, a cDNA fragment derived from Japanese encephalitis virus may be inserted into the restriction enzyme site provided artificially at the downstream of the first vector.

Upon construction of these first and second recombinant vectors, the *Escherichia coli* system which is easy in genetic manipulation may be used. Plasmid vectors to be used are not particularly limited as long as they are suited for the purpose.

In the present invention, genome DNA of Baculovirus is mixed with the second recombinant vector and the mixture is then transfected to insect cells to cause homologus recombination between the vector DNA and virus genome DNA, whereby recombinant Baculovirus is constructed.

The insect culture cell as used herein may be any cell insofar as Baculovirus can grow there. Specific examples include Sf9 cell, derived from *Spodoptera frugiperda*, and the like.

The construction of the recombinant Baculovirus may be carried out in a conventional manner. The procedures can be performed, for example, in a manner similar to the examples of Japanese Patent Application KOKAI No. 37988/1985. That is, the second recombinant vector and Baculovirus genome DNA are transfected to insect cells and the supernatant fluids containing recombinant Baculoviruses are recovered. The fluids containing recombinant Baculoviruses are subjected to standard AcNPV polyhedrin plaque assay described in L.E. Borgman et al. (J. Virol., 19, 820-832, 1976). Plaques that do not form virus occlusions are selected as virus plaques of candidate of the recombinant virus. A virus is recovered from the plaque. As a method for selecting the virus harbouring therein the DNA fragment encoding E protein of Japanese encephalitis virus from these candidate, plaque by hybridization using a DNA probe; alternatively, immunoassay using antiserum or monoclonal antibody may be utilized.

The thus purified recombinant Baculovirus is infected to insect cells susceptible to be infected. The insect cells are cultured under appropriate growth conditions in a conventional manner. After suitable incubation period, the cells are collected and sonicated to prepare an extract. The expression protein is recovered from the extract in an appropriate fashion.

The insect cells used for the incubation are not particularly limited so long as Baculovirus can grow in the cells. The particularly preferred one is Sf9 cell. The Sf9 cells can be cultured under the conditions generally known to the artisan in the art (see, J. Gen. Virol, 36, 361-364 (1977)). Suitable culture conditions can easily be determined by preliminary experiment but, it is preferred to culture in a medium containing 10% fetal calf serum at 28° C. Recovery methods of the expression protein from the cells are not particularly limited so far as they are done through conventional method for biochemical purification, but affinity chromatography using antibodies to Japanese encephalitis virus is the desired one.

Figure 1:
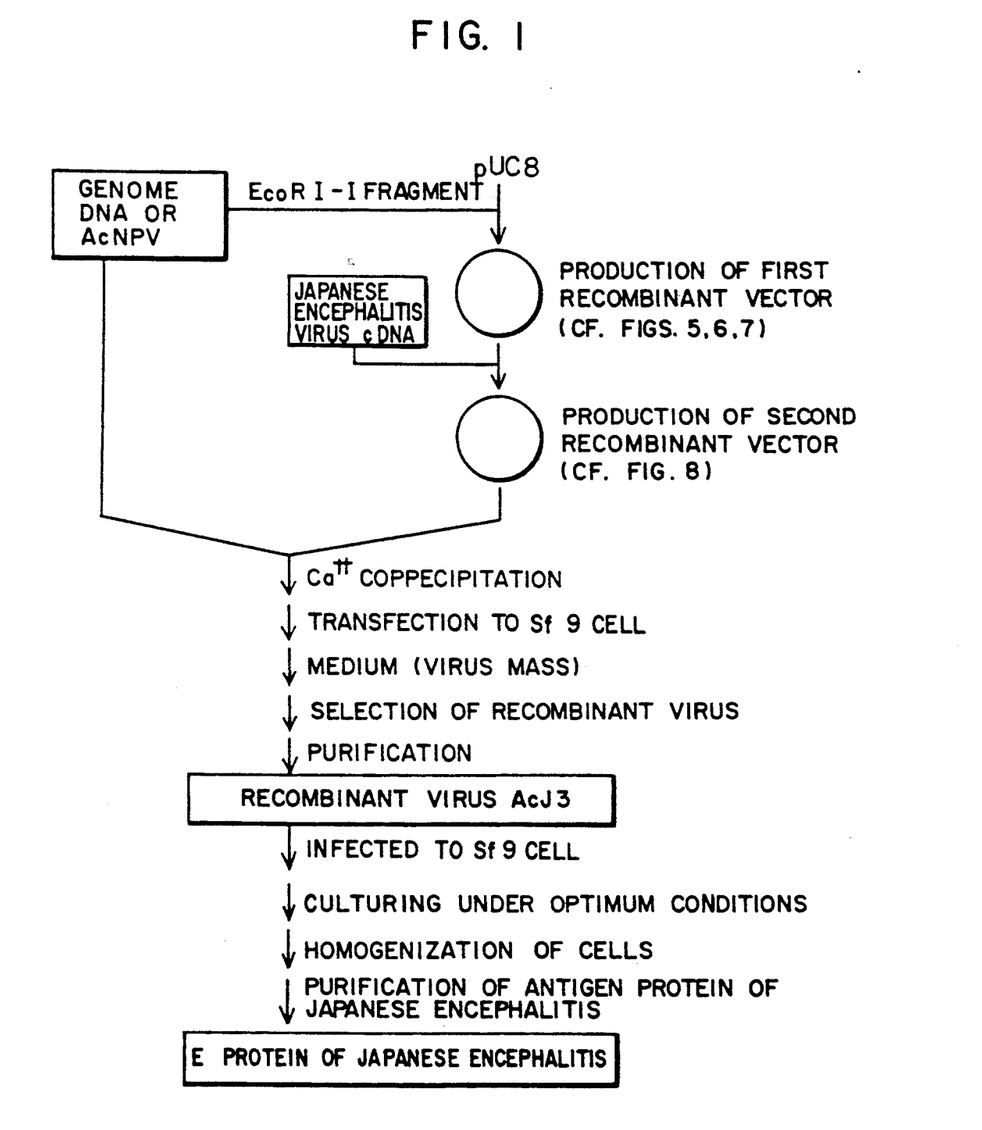
FIG. 1 shows the procedure of the present invention.

As above, the present invention has been described. One of the embodiments of the present invention is outlined in FIG. 1.

According to the present invention, there is thus obtained the recombinant Baculovirus in which the cDNA encoding E protein derived from Japanese encephalitis virus is integrated into the genome region non-essential to proliferation of Baculovirus under control of the promoter; insect cells are infected with the recombinant virus and the infected cells are cultured, whereby E protein of Japanese encephalitis virus can be obtained. This E protein is useful as vaccines or diagnostics. For the preparation of a vaccine preparation, E protein can be diluted with any of conventional diluents and/or carriers in the conventional manner. The application dose of such vaccine can be determined according to the conventional manner; however, it would be sufficient to administer it in an amount capable of producing antibody having a titer of 1.0 to 1.0 ($log_{10}$) in blood.

(EXAMPLES)

Hereafter the present invention will be described in more detail with reference to the examples below.

Example 1

Production of cDNA encoding E protein of Japanese encephalitis virus (1) Extraction of RNA genome from Japanese encephalitis virus Mosquito-derived established cell C6/36 (J. Gen. Virol., 40, 531-544 (1978)) were infected with Japanese encephalitis virus Sagayama strain. After the viruses were proliferated, the culture supernatant was mixed with polyethylene glycol. The mixture was centrifuged to purify Japanese encephalitis viruses. After extraction from the purified viruses with phenol, ethanol was added to the extract to cause precipitation, whereby virus genome RNA (about 11 Kbp) are isolated from said extract.

Figure 2:
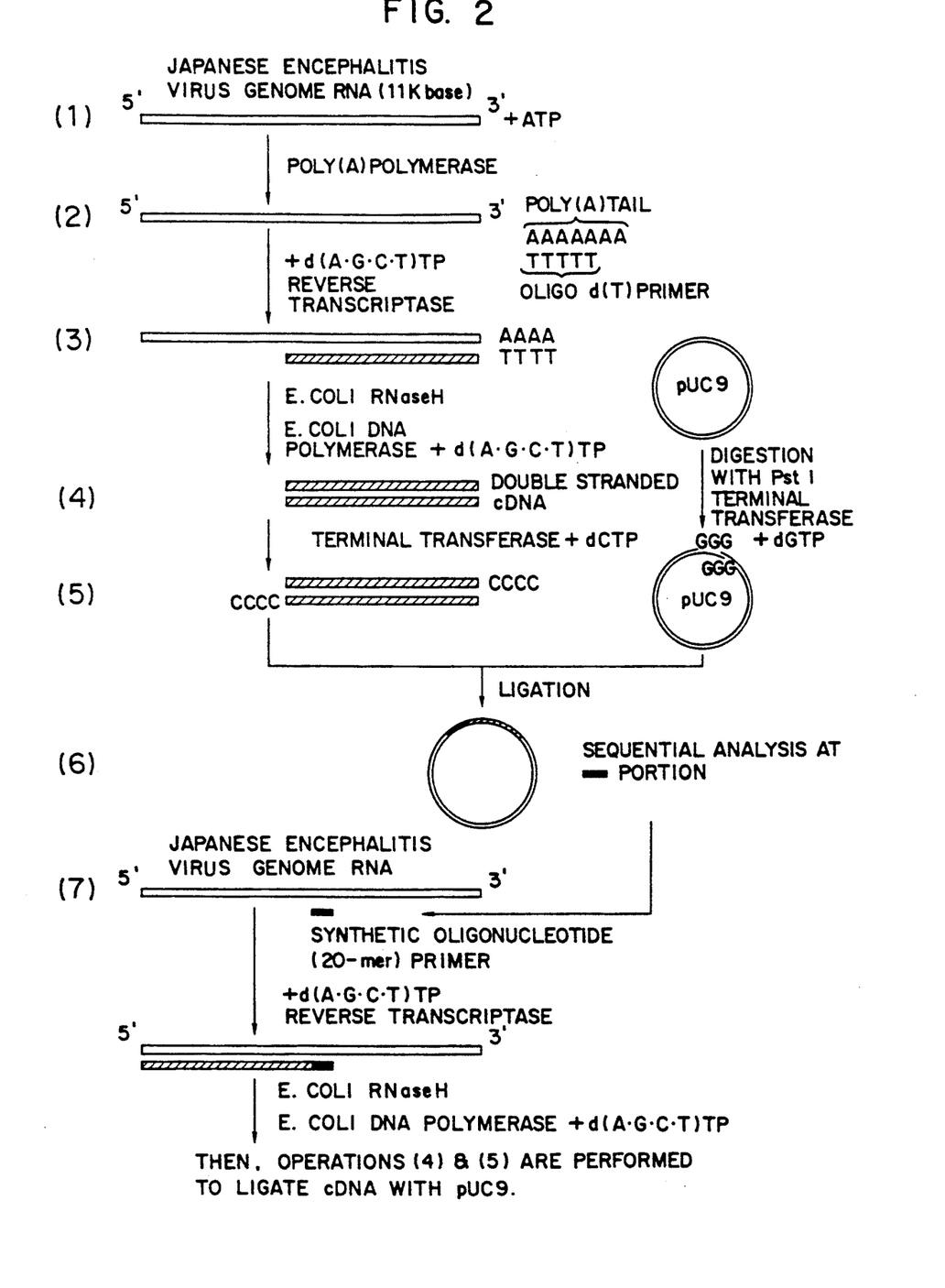
FIG. 2 shows the procedure for cloning of cDNA of Japanese encephalitis virus.

(2) Cloning of cDNA of Japanese encephalitis virus (cf. FIG. 2):

Using poly(A) polymerase (Takara Shuzo Co., Ltd.), poly(A) was added to the virus genome RNA prepared in (1) and this is used as a template: 4 kinds (A, G, C, T) of deoxyribonucleoside triphosphates were reacted with reverse transcriptase using oligo dT as a primer to synthesize first strand cDNA. Next, double stranded cDNA was constructed using E. coli RNase H and 4 kinds (A, G, C, T) of deoxyribonucleoside triphosphates and E. coli DNA polymerase (Molecular Cloning [Cold Spring Harbor Lab., (1982)], p. 211-246) and, dC chain was added using terminal transferase. On the other hand, after digesting plasmid pUC9 (manufactured by Pharmacia Fine Chemicals) with restriction enzyme Pst I, dG chain was added to the digestion product by terminal transferase. The dG chain-added product was mixed with the cDNA described above. The mixture was subjected to ligation to cyclize. This recombinant plasmid was transfected into E. coli HB101 competent cell to obtain a transformant. A plasmid was taken out from the transformant and the length of insert cDNA was compared on agarose gel. With respect to the longest insert cDNA, a sequence at the 5'-end was analyzed (Gene, 19, p. 269 (1982)). Based on the results of sequential analysis, cDNA was again constructed by the method described above using 20-mer synthetic oligonucleotide (5'-dATTCCGTACCATGCAGT-CCA-3') as a primer and virus genome RNA as a template. The cDNA was ligated with plasmid pUC9 to obtain a number of transformants. From the obtained transformants, a transformant containing a recombinant plasmid bearing cDNA encoding the objective envelope protein was screened by a method described below.

With respect to a method for constructing cDNA clone of Japanese encephalitis virus, an example of constructing cDNA clone of Japanese encephalitis virus using Japanese encephalitis virus JaOArS 982 strain in a similar manner is described in Gene, 48, p. 195-201 (1986).

(3) Screening of recombinant plasmid pJE4118 containing cDNA (4118) encoding envelope protein of Japanese encephalitis virus (cf. FIGS. 2 and 3):

The transformants obtained in (2) were grown on agar plate and replicated onto a nitrocellulose filter. After gently washing the replicated filter with 0.2% NP-40 (surfactant, Nakarai Kagaku), the filter was subjected to immunoscreening using anti JE serum. One transformant capable of positively reacting was obtained, while the reactivity was weak. A plasmid possessed by the transformant was named pJE4118. Then, plasmid pJE4118 was prepared in a conventional manner (Molecular Cloning, p. 75-95, [supra]) and cDNA inserted into plasmid pUC9 was excised with restriction enzyme Pst I. Using this cDNA as a DNA probe, the various transformants obtained in (2) were subjected to screening by the colony hybridization method (Molecular Cloning, p. 382-387 [supra]). A plasmid bearing cDNA overlapping with the insert cDNA (4118) of pJE4118 was selected. The thus selected cDNA (2-20) was recovered from the plasmid and its positional relationship was determined by restriction enzymes (cf. FIG. 3). It was thus made clear that cDNA (2-20) partially overlapped with the N-terminal of cDNA (4118).

(4) Analysis of the base sequence of cDNA encoding envelope protein (cf. FIG. 4):

Recombinant plasmids pJE4118 and pJE2-20 were cleaved with restriction enzyme Pst I to give DNA fragments of about 2.5 Kbp and about 1.0 Kbp, respectively. With respect to these fragments, their sequences were analyzed by the method of Messing et al. using M13 phage (Gene, 19, p. 269 (1982); Science, 241, p. 1205 (1981)), from in order the 5'-end in the case of cDNA (4118) and from the 3'-end in the case of cDNA (2-20).

As the result, it has been noted that the cDNA sequence at portions where both were overlapping was 334 bases from the third codon of the 5th amino acid to the 116th amino acid in FIG. 4. Based on the comparison of the amino acid sequence expected from this base sequence with the amino acid sequence of E protein of yellow fever virus (akin to and belonging to the same genus as in Japanese encephalitis virus) already known (Science, 229, 726–733 (1985)), it has been deduced that E protein of Japanese encephalitis virus is the amino acids from +1st to the 500th shown in FIG. 4.

Likewise, it has been deduced that M protein of Japanese encephalitis virus is the amino acids from the −75th to the −1st and, preM protein is the amino acids from the −167th to the −76th as shown in FIG. 4. Furthermore, it has been deduced that the upstream of preM protein encodes a part of C protein of Japanese encephalitis virus.

Figure 3:
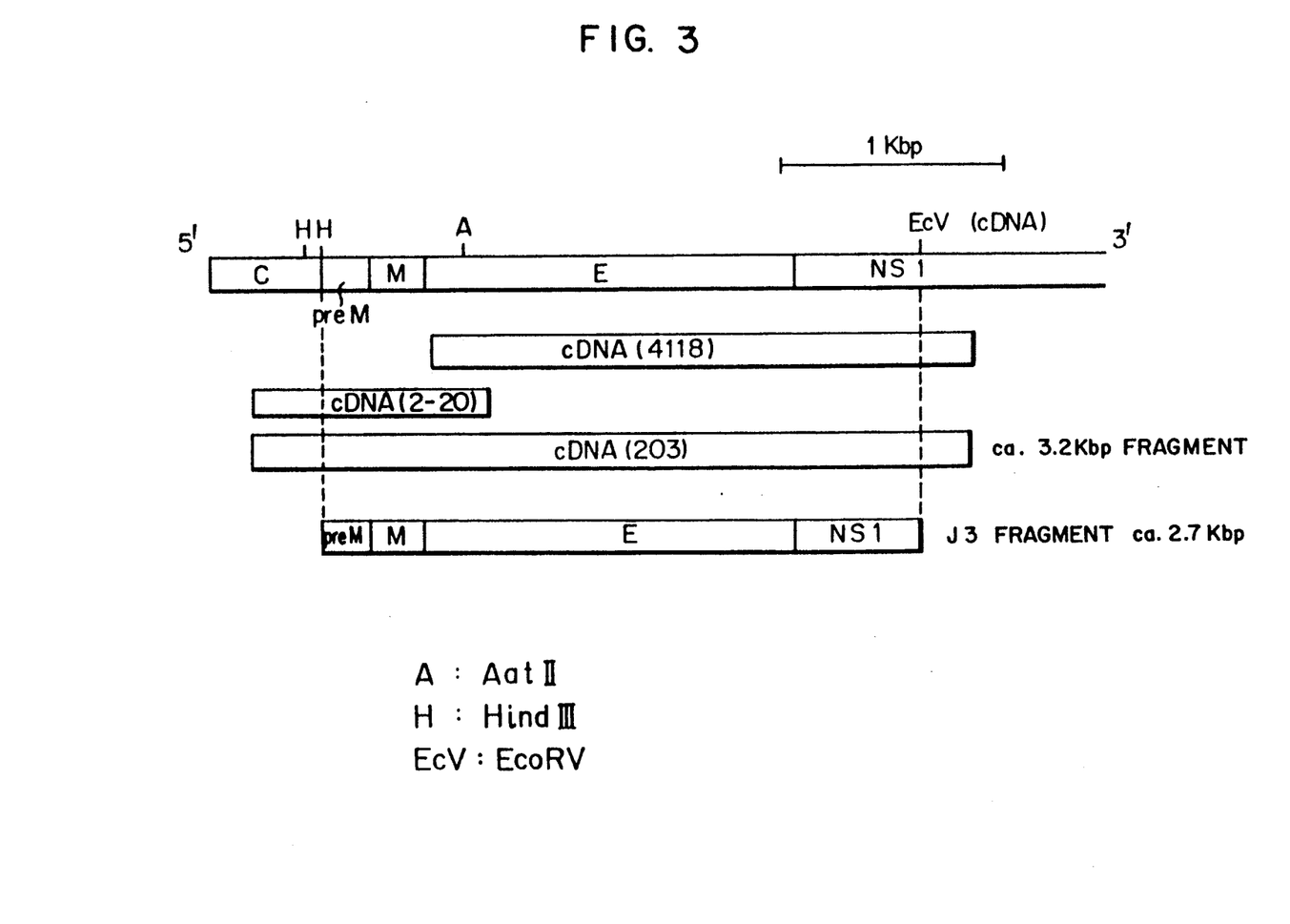
FIG. 3 indicates a positional relation of restriction enzyme sites in cDNA.

(5) Construction of cDNA encoding envelope protein of Japanese encephalitis virus (cf. FIGS. 3 and 4):

cDNA (4118) is deleted of bases encoding 5 amino acids at the N-terminal of E protein. Thus, spliced cDNA (2-20) was jointed with cDNA (4118) at the Aat II site to obtain cDNA (203) covering full E protein region.

Then, cDNA (203) was treated with Hind III and EcoR V to recover about 2.7 Kbp of cDNA fragment (J3). This fragment contains the region for encoding M protein and preM protein, in addition to the region for encoding E protein.

Example 2

Figure 5:
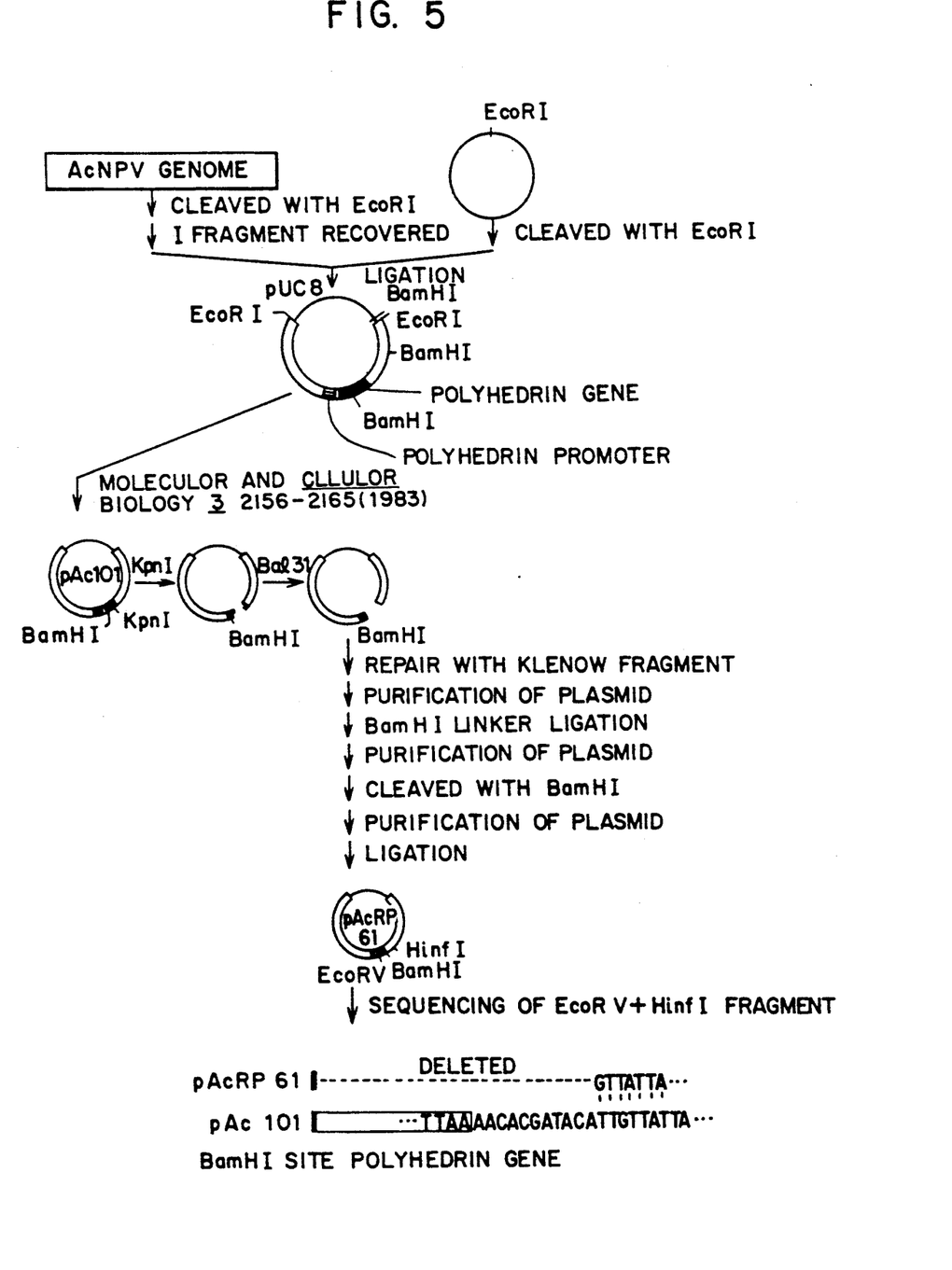
FIGS. 5 through 7 show the procedures for constructing the first recombinant vector pAcYMS1.

Production of the first recombinant vector pAcYMS1 having integrated therein the DNA region non essential to proliferation of Baculovirus (cf. FIGS. 5 through 7):

(1) Production of plasmid pAcRP61 wherein 3'-end of polyhedrin gene is deleted (cf. FIG. 5)

In order to constitute the first recombinant vector, the DNA fragment containing polyhedrin gene of AcNPV (wild strain) was cloned to plasmid pUC8 at the EcoR I site. DNA of AcNPV was purified by extracting from the virus followed by equilibrated centrifugation in cesium chloride density gradient, as explained by G.E. Smith and M.D. Summers (Virology, 89, 517–527, 1978). Next, this DNA was fully digested with restriction enzyme EcoR I. After 7.3 Kbp of the EcoR I-I fragment was recovered by agarose gel, the fragment was cloned to pUC8 at the EcoR I site to prepare pAcEcoR I-I. This recombinant plasmid pAcEcoR I-I has 3 BamH I recognition sites (cf. FIG. 5). One is in the polyhedrin gene, one is far downstream the polyhedrin gene and the last one is in polylinker of pUC8. The latter two BamH I recognition sites were removed from pAcEcoR I-I in a manner similar to the method described by G.E. Smith et al. (Molecular and Cellular Biology, 3, p. 2156-2165, 1983) to produce pAc101.

Next, pAc101 was cleaved at the Kpn I site present in the polyhedrin gene and sequentially deleted from the terminal using 0.5 unit of Bal 31 exonuclease. Thereafter, the terminals of it were repaired using E. coli DNA polymerase (Klenow fragment). The plasmid DNA was purified and 0.5 μg of phosphorylated BamH I linker (5'-pCGGATCCG-3') was added to 100 μl of the reaction mixture, together with 10 units of T4 DNA ligase. After incubation at room temperature for 2 hours, the DNA was purified. Then, the DNA was again digested with BamH I in 100 μl of the reaction solution. The digested DNA was subjected to 0.7% agarose gel electrophoresis and then recovered to purify it. After ligation of the DNA using T4 DNA ligase, E. coli JM109 cells were transformed by the ligated DNA (ampicillin resistance). From several transformants, plasmids were prepared. With respect to fragments excised from the respective plasmids with EcoR V and Hinf I, sequence analysis was performed by the method of Messing et al. (Gene, 19, p. 269, 1982). It was found that one of the fragments had a deletion in the bases from just after the end of the bases for the Bam HI linker up to the 13th base downstream from the translation termination codon of the polyhedrin gene, as shown in FIG. 5. The plasmid was named pAcRP61 (FIG. 5).

Figure 6:
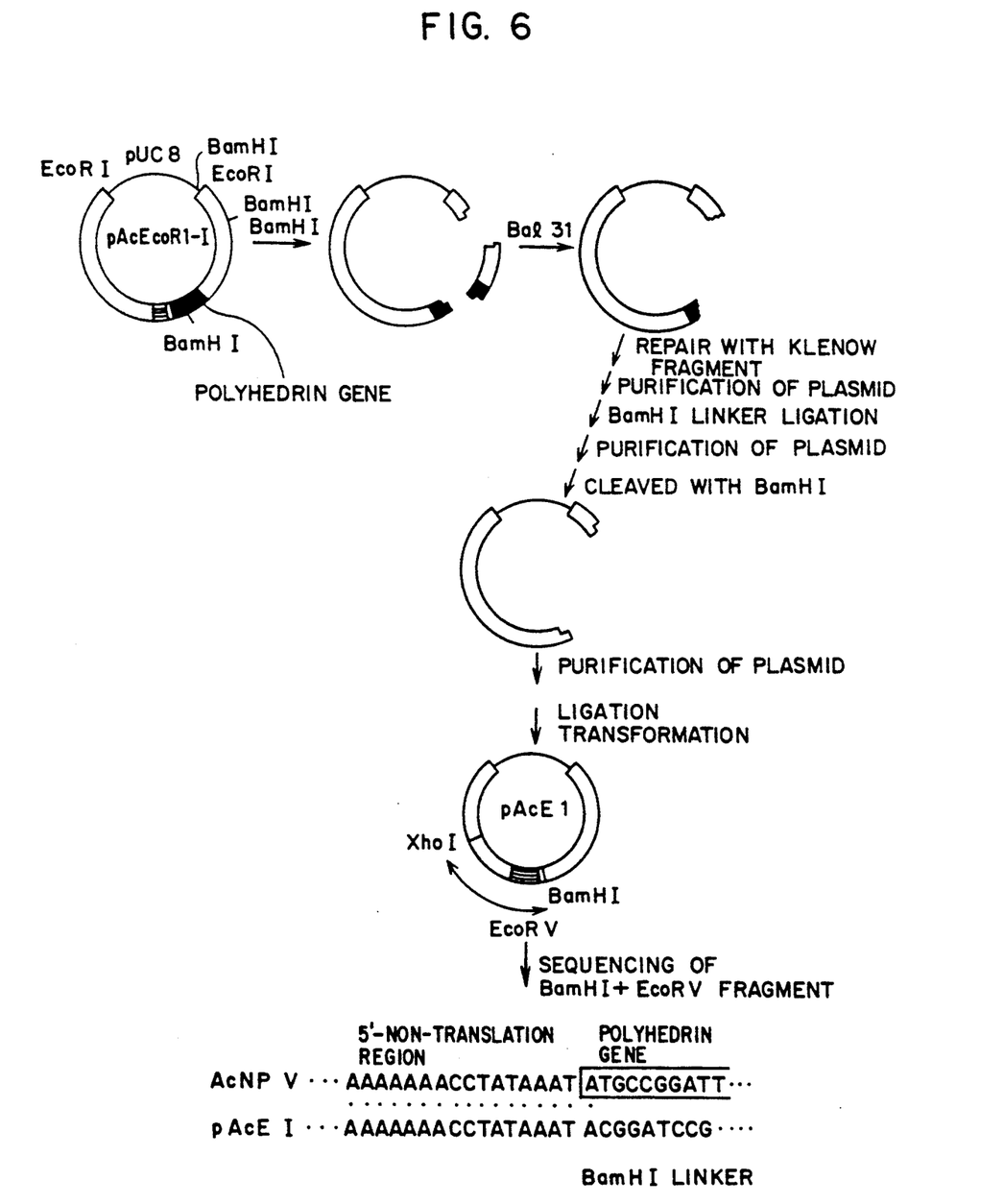

(2) Production of plasmid pAcE1 wherein polyhedrin gene is deleted (cf. FIG. 6)

pAcEcoR I-I was cleaved with BamH I, and deleted from the end of the strand using 0.5 unit of Bal 31 exonuclease. Thereafter, the ends were repaired using E. coli DNA polymerase (Klenow fragment). The plasmid DNA was purified and the aforesaid phosphorylated BamH I linker was added to the reaction mixture, together with T4 DNA ligase. After incubation at room temperature for 2 hours, the DNA was purified. Then, the DNA was again digested with BamH I in 100 μl of the reaction solution. The digested DNA was subjected to 0.7% agarose gel electrophoresis and then recovered to purify it. After ligation of the DNA using T4 DNA ligase, E. coli JM109 cells were transformed by the ligated DNA (ampicillin resistance). From several transformants, plasmids were prepared. With respect to fragments excised from the respective plasmids with EcoR V and BamH I, sequence analysis was performed. From a number of plasmids, a plasmid containing the fragment deleted up to T of translation initiation codon (ATG) of the polyhedrin gene was selected. The plasmid was named pAcEl (FIG. 6).

Figure 7:
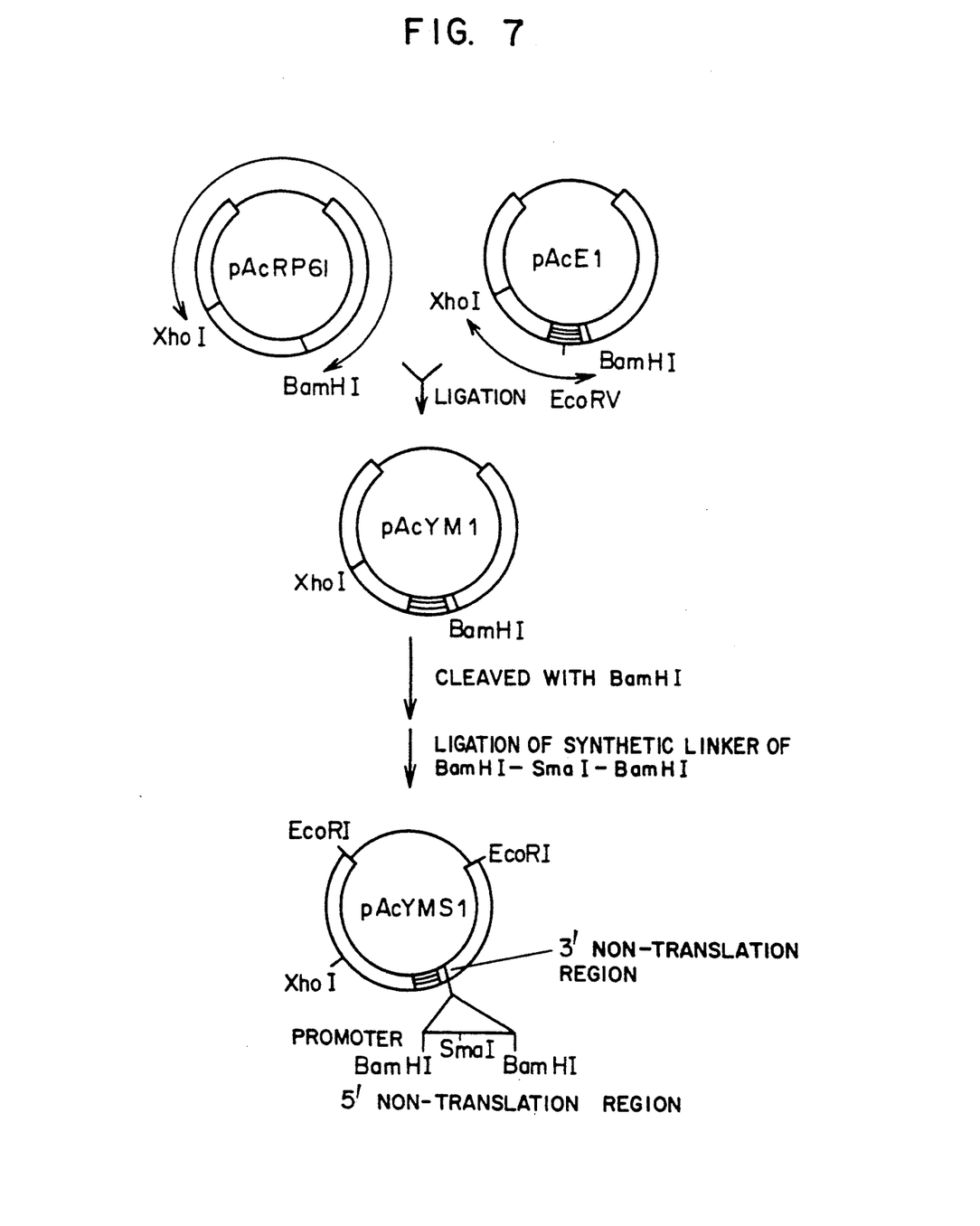

(3) Production of the first recombinant vector plasmid pAcYMS1 (cf. FIG. 7)

The previously obtained pAcRP61 was cleaved with Xho I and BamH I. The longer fragment shown with arrows in FIG. 7 was subjected to 0.7% agarose gel electrophoresis and then recovered. On the other hand, pAcEl was cleaved with Xho I and BamH I. The shorter fragment shown with arrows in FIG. 7 was subjected to 0.7% agarose gel electrophoresis and then recovered. These two fragments were ligated using T4 DNA ligase. The thus obtained plasmid was named pAcYM1. Next, pAcYM1 was cleaved with BamH I, at which site a synthetic linker (5'-pGATCCCCGGG-3') of BamH I-Sma I-BamH I was inserted. The thus produced plasmid was named pAcYMS1 (cf. FIG. 7). The pAcYMS1 contains in the EcoR I-I fragment, in succession, polyhedrin promoter, the 5' non-translational region of polyhedrin gene, the BamH I-Sma I-BamH I restriction enzyme site and the 3' non-translational region of polyhedrin gene.

Example 3

Figure 8:
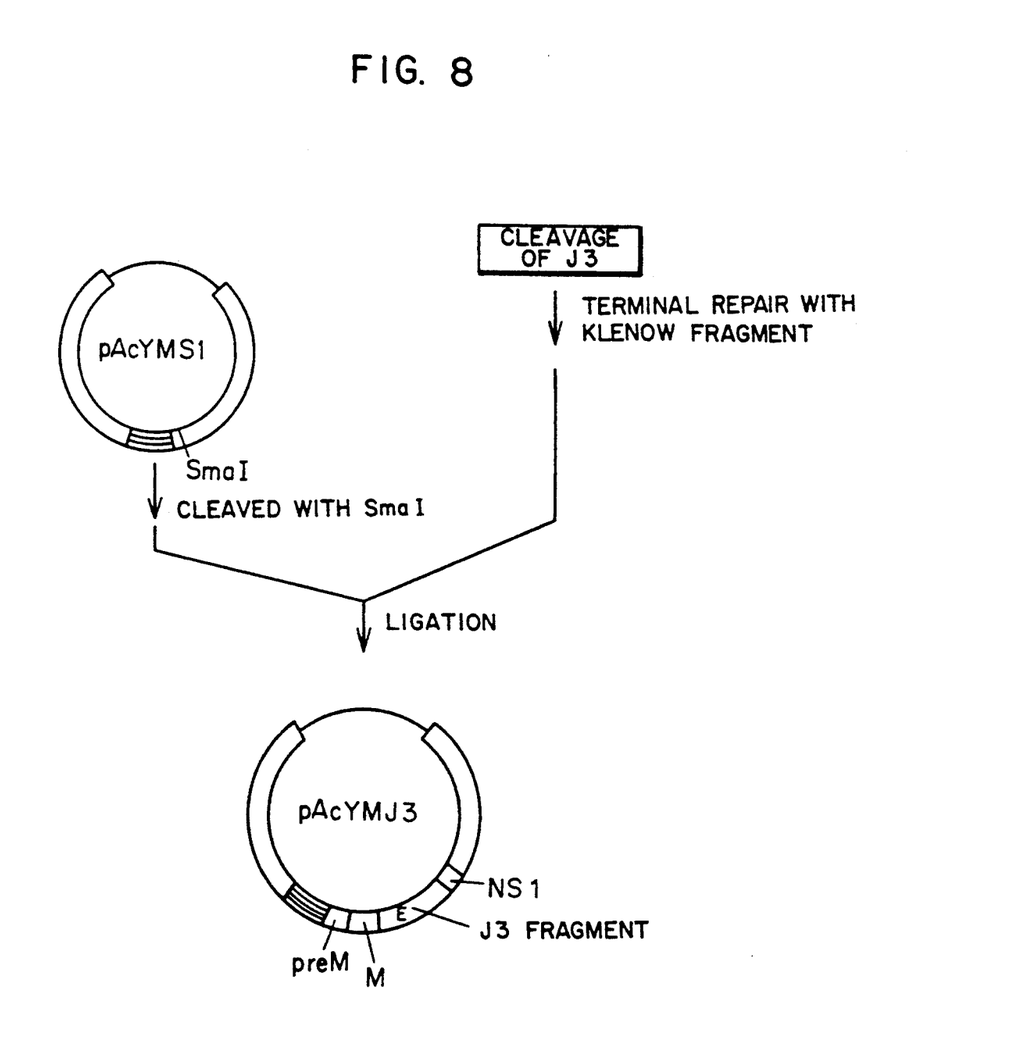
FIG. 8 shows the procedures for constructing the second recombinant vector pAcYMJ3 containing cDNA encoding E protein.

Production of the second recombinant vector having cDNA encoding E protein of Japanese encephalitis virus (cf. FIG. 8)

After the terminals were repaired using *E. coli* DNA polymerase (Klenow fragment), cDNA (J3) obtained in Example 1, (5) was ligated with pAcYMS1 which was cleaved with restriction enzyme Sma I using T4 DNA ligase. Then, JM109 was transformed. Plasmids were purified from several transformants. The plasmid in which cDNA (J3) described above had been integrated at the Sma I site of pAcYMS1 in the positive direction (when the translation direction of cDNA is directed to the same direction of transcription of polyhedrin promoter, it is termed the positive direction) is selected based on the results of cleavage pattern using suitable restriction enzymes. The thus obtained second recombinant vector was named pAcYMJ3.

Example 4

Construction of recombinant Baculovirus

In a manner similar to the process described in the monograph of F.L. Graham et al. (Virology, 52, p. 456–467, 1973), 1 μg of genome DNA of AcNPV was mixed with 1 to 10 μg of pAcYMJ3. The mixture was diluted with 1-HEPES (N-2-hydroxyethylpiperazine-N'-2-ethanesulfonate) buffer (pH 7.0) containing 15 μg/ml calf thymus DNA to 950 μl. While stirring the mixture, 50 ml of 2.5 M $CaCl_2$ was dropwise added thereto to form precipitates at room temperature for 30 minutes. The precipitated DNA, 1 ml, was added to Sf9 cells in 2 ml of medium charged in a 60 ml culture plate. The cell monolayer was washed with the medium 4 hours later and 2 ml of medium containing 10% fetal calf serum was added thereto followed by incubation for 3 days. Thereafter, the medium was collected with a sterile pipette. In this medium, recombinant and non-recombinant AcNPVs were mixed. In order to isolate recombinant AcNPV from the mixture, the collected medium was appropriately diluted and the dilution was infected to the Sf9 monolayer cultured cells to form plaques. The plaque in which no virus occlusion was formed was selected and the virus was recovered from the plaque. The virus was suspended in PBS. A part of the suspension was spotted on a nylon or nitrocellulose membrane for dot hybridization and a part of the suspension was reinfected to Sf9 cells to proliferate the virus.

After the treatment with 0.5N NaOH for 10 minutes and with 1M Tris-hydrochloride buffer for 5 minutes was repeated 3 times, the spotted membrane was treated with 1.5M NaCl and 0.5M Tris-hydrochloride buffer for 5 minutes. The treated membrane was saturated with 2-fold SSC (1-fold SSC: 0.15M NaCl, 0.015M sodium citrate) followed by annealing at 80° C. for 2 hours. Then, treatment was performed with 4-fold SET (0.6M NaCl, 0.08M Tris-Cl, 4 mM EDTA (pH 7.8))-10-fold Denhardt-0.1% SDS at 68° C. for 2 hours. 4-Fold SET-10-fold Denhardt-0.1% SDS-0.1% $Na_4P_2O_7$-50 μg/ml-modified salmon sperm DNA and Japanese encephalitis virus E protein cDNA labeled with $^{32}P$ were hybridized by nick translation at 68° C. for 14 hours. After washing, the membrane was put on an X ray film, which was subjected to autoradiography and an exposed spot on the film was selected. The virus solution corresponding to the exposed spot was again diluted suitably and the dilution was infected to Sf9 cells to develop plaques. The developed plaques were treated as above and the procedure for purification was repeated until the developed plaques were all positive by dot hybridization. The thus obtained virus was the objective recombinant Baculovirus and named AcJ3.

Example 5

Production of Japanese encephalitis virus E protein by recombinant Baculovirus:

Sf9 cells were grown in monolayer to reach a density of $5 \times 10^6$/ml. The growth medium was removed and a medium containing 5 p.f.u./cell of AcJ3 was supplemented to cause infection at 23° C. After the infection, the cells were cultured for 2 days to express E protein of Japanese encephalitis virus in the infected cells. The expression protein was confirmed by Western blotting method (Bernet, W.N., Analyt. Biochem., 112, p. 195–203, 1981) using antisera to E protein. The results reveal that the infected cells of AcJ3 produced a protein having a molecular weight of about 53000 daltons. The molecular weight of 53000 daltons is the same as that of the one presumed from the amino acid sequence of E protein of Japanese encephalitis virus (FIG. 4).

In spite that preM, M and a part of NS1 (non-structural protein) were contained in addition to E in cDNA (J3) integrated into AcJ3 genome, the protein of 53000 daltons is expressed. From this fact, it is easily assumed that the protein expressed in the infected cells would be subject to processing similar to E protein of Japanese encephalitis virus to be E protein of 53000 daltons. The E protein expressed in the infected cells of AcJ3 is reactive with antisera to E protein of Japanese encephalitis virus and it is thus clear that the expressed E protein has antigenicity. Therefore it can be used for vaccines or diagnostics. The E protein produced in the infected cells is able to be detected in the Western blotting method previously mentioned even though the E protein is detected from the cell extracts of only 200 infected cells. It is thus understood that E protein is produced on a considerable level. Instead of AcJ3, wild Baculovirus was likewise infected to cells of Sf9 cells to examine the protein in the cells. However, no protein reactive with antisera was detected.

Example 6

Animal immunity experiment with Japanese encephalitis virus E protein expressed by recombinant Baculovirus:

$4 \times 10^7$ Sf9 cells were cultured in monolayer. After the growth medium was removed, a medium containing 5 p.f.u./cell of AcJ3 was supplemented to cause infection at 23° C. After the infection, the cells were cultured for 2 days to express E protein of Japanese encephalitis virus in the infected cells. Then, the infected cells were harvested by centrifuging at 3,000 rpm for 20 minutes. The thus harvested cells were washed with 1 ml of PBS buffer and sonicated. The supernatant obtained by centrifuging at 3,000 rpm for 20 minutes was taken as a test sample for animal immunity.

Four male mice of C3H/He at the age of 4 weeks (obtained from Shizuoka Experimental Animals Cooperation) were inoculated intraperitoneally with 0.1 ml of the above-mentioned test sample containing E protein, respectively. Two weeks later, two of them were bled. The rest of them were boosted with 0.1 ml of the same test sample and then bled a week later. A serum was taken from the collected blood in a conventional manner and the neutralizing antibody titer against Japanese encephalitis virus in the serum was measured in such a manner as described in "Tissue Culture Technique for Virus Test" (authored by Takashi KITAMURA, published by KINDAI Inc., p. 250–255). The results of the measurement are shown in Table 1.

TABLE 1

| Mouse No. | Booster | Neutralizing Antibody Titer in the Blood of the Mouse ($\log_{10}$) |
| --- | --- | --- |
| 1 | − | 1.2 |
| 2 | − | 1.1 |
| 3 | + | 1.5 |
| 4 | + | 1.8 |
| Control | − | <0.6 |

*The value in the above table is one that a neutralizing antibody titer in the blood of the mouse is transformed according to common logarithms.

As apparent from the results, the inoculation of Japanese encephalitis virus E protein produced by recombinant Baculovirus AcJ3 raised the neutralizing antibody against Japanese encephalitis virus in the blood of animal. Accordingly, the efficacy as a vaccine is proved.

While the invention has been described in detail and with reference to specific embodiments thereof, it is apparent to one skilled in the art that various changes and modifications can be made therein without departing from the spirit and the scope of the present invention.

What is claimed is:

1. A recombinant Baculovirus comprising cDNA encoding envelope protein of Japanese encephalitis virus, cDNA encoding membrane protein of Japanese encephalitis virus, and cDNA encoding premembrane protein of Japanese encephalitis virus, and cDNAs being inserted into a genome region of said Baculovirus non-essential to proliferation of said Baculovirus.

2. The recombinant Baculovirus according to claim 1, wherein said cDNA encoding said envelope protein of Japanese encephalitis virus encodes the amino acid sequence of the envelope protein shown in FIG. 4.

3. The recombinant Baculovirus according to claim 1, wherein said cDNAs are inserted downstream of and are operably linked to a promoter in said genome region.

4. The recombinant Baculovirus according to claim 1, wherein said cDNAs are inserted downstream of and are operably linked to a promoter of polyhedrin gene of Baculovirus or a promoter of 10K polypeptide gene of Baculovirus.

5. The recombinant Baculovirus according to claim 1, wherein said cDNAs are inserted downstream of and are operably linked to a promoter of polyhedrin gene of Baculovirus.

6. The recombinant Baculovirus according to claim 1, wherein said cDNAs are inserted between a translation initiation codon and a translation termination codon under the control of a promoter.

* * * * *